United States Patent [19]
Weyers et al.

[11] Patent Number: 5,925,015
[45] Date of Patent: Jul. 20, 1999

[54] NUTRITIONAL SUPPORT SYSTEM

[75] Inventors: Richard G. Weyers, Los Altos; Atul D. Ayer, Palo Alto; Brenda J. Pollock, Cupertino; Brian L. Barclay, Sunnyvale; Ernest S. Quan, Fremont, all of Calif.

[73] Assignee: ALZA Corporation, Palo Alto, Calif.

[21] Appl. No.: 08/859,627

[22] Filed: May 20, 1997

Related U.S. Application Data

[60] Provisional application No. 60/018,314, May 24, 1996, provisional application No. 60/019,205, Jun. 6, 1996, and provisional application No. 60/038,539, Feb. 28, 1997.

[51] Int. Cl.$^6$ .................................................. A61M 37/00
[52] U.S. Cl. ........................ 604/84; 424/465; 604/890.1
[58] Field of Search .................... 424/472, 473, 424/474, 465; 604/251, 253, 82–85, 890.1, 891.1

[56] References Cited

U.S. PATENT DOCUMENTS

| | | | |
|---|---|---|---|
| 3,916,899 | 11/1975 | Theeuwes et al. | 128/260 |
| 4,063,064 | 12/1977 | Saunders et al. | 219/121 |
| 4,088,864 | 5/1978 | Theeuwes et al. | 219/121 |
| 4,200,098 | 4/1980 | Ayer et al. | 128/260 |
| 5,252,338 | 10/1993 | Jao et al. | 424/473 |
| 5,529,787 | 6/1996 | Merrill et al. | 424/472 |
| 5,531,681 | 7/1996 | Walton et al. | 604/84 |
| 5,531,682 | 7/1996 | Mazer et al. | 604/84 |
| 5,531,734 | 7/1996 | Geckle et al. | |
| 5,532,003 | 7/1996 | Wong et al. | 424/473 |
| 5,533,973 | 7/1996 | Piontek et al. | 604/84 |
| 5,603,954 | 2/1997 | Wong et al. | 424/473 |
| 5,660,861 | 8/1997 | Jao et al. | 424/473 |
| 5,702,725 | 12/1997 | Merrill et al. | 424/472 |

OTHER PUBLICATIONS

Lange, Current Medical Diagnosis and Treatment, pp. 1104–1108 (1996).
Cecil, Textbook of Medicine, pp. 1168–1171 (1969).
The Merck Manual of Diagnosis and Therapy, pp. 942–949 (1987).
McGraw–Hill, Inc., Principles of Internal Medicine, pp. 464–472 Physicians' Desk Reference, 50th Edition, p. 2220 (1996).

*Primary Examiner*—Wynn Wood Coggins
*Assistant Examiner*—Sharon Finkel
*Attorney, Agent, or Firm*—Paul L. Sabatine; Susan K. Thomas; Michael J. Rafa

[57] ABSTRACT

A nutritional system is disclosed, for delivering a colorant dye to a nutritional fluid that flows through the nutritional system.

1 Claim, No Drawings

NUTRITIONAL SUPPORT SYSTEM

CROSS-REFERENCE TO RELATED APPLICATIONS

This application claims the benefits of provisional applications Ser. No. 60/018,314 filed May 24, 1996, Ser. No. 60/019,205 filed Jun. 6, 1996, and Ser. No. 60/038,539 filed Feb. 28, 1997.

FIELD OF THE INVENTION

This invention pertains to a delivery system for delivering an identifying agent to a nutritional support formulation. This invention relates also to a combination comprising the delivery system, a reservoir containing a nutritional support formulation and to a drip chamber. The invention pertains additionally to a process of adding an identifying agent to a nutritional support formulation, and to a method for administering a nutritional formulation to a patient.

BACKGROUND OF THE INVENTION

A clinical need exists for: (1) a nutritional system comprising a delivery identification means; (2) for a method for ascertaining if a patient on nutritional support is experiencing medical problems contemporaneously with the nutritional support; and (3) for a method to ensure that a patient is receiving the benefits of nutrition.

Nutritional support is the provision of nutrients to patients who cannot meet their nutritional requirements by eating standard diets. For patients on nutritional support, nutrients may be delivered to the gastrointestinal tract enterally, using oral nutritional supplements, nasogastric and nasoduodenal feeding tubes, and tube enterostomies. Current nutritional support techniques permit adequate nutrient delivery to virtually any patient.

Nutritional support is indicated for many patients, including patients with inadequate bowel syndromes, patients with a severe, prolonged hypercatabolic status, patients with extensive burns, multiple trauma and mechanical ventilation, patients requiring prolonged therapeutic bowel rest, patients with a treatable disease who have sustained a loss of over 25% body weight, patients with a functioning gastrointestinal tract (as a supplemental oral diet), and patients with other conditions, such as neurological disorders, recovering from surgery and clinical conditions, such as malabsorption disorders associated with Crohn's disease.

Nutritional support has enjoyed wide acceptance in medicine, and it is used daily in clinics, hospitals and nursing homes. While nutritional support is used to deliver many nutrients, problems are frequently associated with its use. For example, if an attending physician detects fluid in the lungs of a patient, the physician needs to know the nature and/or the content of the fluid, and consequently sucks fluid from the lungs to ascertain the origin of the fluid, in order to prescribe a mode of treatment. To effect a treatment, it is necessary to know if the fluid is stomach fluid that has been regurgitated up the esophagus and aspirated down the trachea into the lungs, fluid from an internal bleeding source, fluid that is infectious in origin, or fluid from a nutritional support system. Nutritional support and internal nutritional support are discussed in *Current Medical Diagnosis and Treatment,* Lange, pp. 1104–1108 (1996); *Textbook of Medicine,* Cecil, pp. 1168–1171 (1969); *The Merck Manual of Diagnosis and Therapy,* pp. 942–949 (1987); and *Principles of Internal Medicine,* pp. 466–472 (1994).

In light of the above presentation, it will be appreciated by those versed in the nutritional support art to which this invention pertains that a pressing need exists for means for ascertaining the presence of a nutritional support fluid administered to a patient to distinguish the nutritional support fluid from biological and infectious fluids. The pressing need exists, also, for a delivery system that delivers an identification to a nutritional support fluid that imparts a distinctive property to the nutritional support fluid.

OBJECTS OF THE INVENTION

Accordingly, in view of the above presentation, it is an immediate object of the invention to provide a nutritional support system for administering a nutritional formulation to a patient, indicated for better health.

Another object of the invention is to provide a nutritional support system comprising a delivery system that delivers an identifying agent to a nutritional support composition.

Another object of the invention is to provide a delivery system that delivers an identifying agent to a nutritional support formulation.

Another object of the invention is to provide a nutritional support system comprising a reservoir, a drip chamber, and a delivery system in the drip chamber for delivering a dye to a nutritional formulation that enters the drip chamber.

Another object of the invention is to provide a drip chamber for ascertaining the flow rate therethrough containing a delivery system that makes available a nontoxic dye to a nutritional fluid formulation that enters and leaves the drip chamber.

Another object of the invention is to provide a delivery system comprising a dye for adding to a nutritional formulation.

Another object of the invention is to provide a composition of matter for use in a delivery system and in a nutritional support formulation system.

Another object of the invention is to provide a method for adding means for identifying a nutritional support formulation by adding a pharmaceutically acceptable dye thereto.

Another object of the invention is to provide a method for adding a dye to a nutritional support formulation that comprises a reservoir of the nutritional formulation, a drip chamber, and a tube for feeding a person in need of nutritional support.

Another object of the invention is to provide a method for administering a nutrient to a patient by a nutritional support system.

Other objects, features and advantages of this invention will be more apparent to those versed in the nutritional support art from the following detailed specification and the accompanying claims.

DISCLOSURE OF EXAMPLES OF THE INVENTION

The following examples are illustrations of the present invention and should not be considered as limiting the scope of the invention, as these examples and other equivalents thereof will become apparent to those versed in the nutritional support art in light of this disclosure and accompanying claims.

EXAMPLE 1

A delivery system for delivering a pharmaceutically acceptable dye to a nutritional support formulation is made as follows: First, 250 mg of FD&C Blue Dye No.1 (Food and Drug Administration, drug and cosmetic acceptable dye) is blended with 145 mg of mannitol, 60 mg of osmotically effective potassium chloride, 15 mg of hydroxypropylmethylcellulose of 11,200 number-average molecular weight, and 25 mg of hydroxypropylcellulose of 40,000 number-average molecular weight, with all the ingredients blended to yield a homogenous mass. Then, ethanol is added to the mass and the blending is continued for 15 minutes to yield a wet mass. The fresh mass is screened and dried in an oven for 24 hours at 50° C. to yield granules. Next, the dry granules are mixed with 5 mg of a lubricant, such as magnesium stearate or stearic acid, and pressed into dye-identification cores to provide the identifying agent. A compressed core that weighs 500 mg is produced by this example.

Next, the cores are coated with a semipermeable wall. The wall-forming composition comprises 20.8 mg of cellulose acetate having an acetyl content of 39.8%, 4.16 mg of poly(vinyl pyrrolidone) of 40,000 number-average molecular weight, and 1.04 mg of polyethylene glycol of 3,350 viscosity-average molecular weight. The wall-forming composition is applied as 4% solid content from an acetone:methanol (80:20 v:v) solution. A pan coater is used to apply the wall around the cores. The solvent is evaporated in an oven at 50° C. for 65 hours and cooled to a room temperature of 72° F. Then, two 25 mil exit passageways are drilled in the wall to yield the delivery system. The delivery system delivers the pharmaceutically acceptable dye for 24.6 hours.

EXAMPLE 2

The procedure of the above example is followed, with all conditions as described, except in this example the dye is FD&C Blue Dye No. 1 blended with a hydroxypropylalkylcellulose of 9,200 to 125,000 number-average molecular weight, a hydroxyalkylcellulose of 10,000 to 75,000 number-average molecular weight and an osmotic solute, such as osmagents sodium chloride, lithium sulfate, sodium sulfate or urea.

EXAMPLE 3

The procedure of the above example is followed in this example, except in this example the FD&C is a member selected from the group consisting of: aniline, nitroso, nitro, azo, oxazin, thiazine, pyrazolone, xanthene, indigoid, anthraquinone, acridine, rosanilin, phthalein and quinoline dyes; and the dye is a member selected from: green, brown, orange, purple, magenta and the like. The amount of dye in a delivery system is from 1 to 750 mg.

EXAMPLE 4

The procedure of Example 1 is followed in this example, with the delivery system delivering the dye to a nutritional support formulation, wherein the nutritional support formulation comprises a gastrointestinally acceptable fluid, such as water, an oil, a protein, a mineral, a saccharide, and a vitamin. Representative of nutritional components include: water, maltodextrin, soy protein, sugar, vegetable oil, sodium caseinate, soy fiber, triglyceride, coconut oil, calcium phosphate, tartaric acid, ester of monodiglyceride, ascorbic acid, calcium carbonate, magnesium phosphate, carrageenan, choline chloride, taurine, ferrous sulphate, zinc sulfate, sodium chloride, alpha-tocopherol acetate, niacinamide, calcium pantothenate, beta-carotene, cupric sulphate, manganese sulfate, thiamine chloride, pyridoxine hydrochloride, riboflavin, vitamin A palmitate, folic acid, biotin, potassium iodide, cyanocobalamin and vitamin D. The nutritional support is described in *Physicians' Desk Reference,* 50th Edition, p. 2220 (1996).

EXAMPLE 5

The procedure of Example 1 is followed in this example, wherein the procedure provides a delivery system comprising 1 to 750 mg of a FD&C acceptable colorant; 2 to 50 mg of an osmagent, such as an osmotically effective solute selected from the group consisting of magnesium sulfate, magnesium chloride, sodium chloride, potassium sulfate, potassium chloride, sodium sulfate, lithium sulfate, potassium acid phosphate, calcium lactate, urea, inositol, magnesium succinate, and tartaric acid; 10 to 300 mg of a carbohydrate, selected from the group consisting of carbohydrate, monosaccharide, disaccharide, polysaccharide, mannitol, raffinose, sucrose, glucose, fructose, pentose, hexose, and lactose; 1 to 40 mg of a hydroxypropylalkylcellulose carrier for the dye, selected from the group consisting of hydroxypropylethylcellulose, hydroxypropylisopropylcellulose, hydroxypropylbutylcellulose, hydroxypropylmethylcellulose, hydroxypropylmethylpentylcellulose and hydroxypropylhexylcellulose; 5 to 75 mg of a viscosity regulating agent, selected from the group consisting of hydroxyalkylcellulose, including hydroxypropylcellulose, hydroxymethylcellulose, triethylcellulose, diphenylmethylcellulose and hydroxyoctylcellulose; and 0.5 to 10 mg of a lubricant, selected from the group consisting of stearic acid, magnesium oleate, magnesium stearate, calcium stearate, potassium palmitate, sodium stearate, sodium palmitate and lithium oleate; and wherein the exit means in the semipermeable wall for delivering the dye from the delivery system is a member selected from the group consisting of an orifice, passageway, bore, pore, porous element, hollow fiber, capillary tube, erodible polymer, soluble compound, fluid leachable compound, porous insert, and porous overlay. Passageways and equipment for forming passageways are disclosed in U.S. Pat. Nos. 3,916,899, 4,063,064, 4,088,864, 4,200,098 and 5,252,338.

EXAMPLE 6

A delivery system for delivering a dye-colorant to a fluid nutritional formulation is made as follows: First, 250 mg of FD&C Blue Dye No. 1 is blended with 145 mg of mannitol, 60 mg of potassium chloride, 15 mg of hydroxypropylmethylcellulose of 11,200 number-average molecular weight, and 25 mg of hydroxypropylcellulose of 40,000 number-average molecular weight, and all the ingredients are blended to yield a homogenous mass. Then, ethanol is added to the mass and the blending continued to yield a wet mass. The wet mass is screened and dried to granules. The granules are mixed with 5 mg of the lubricant magnesium stearate, and cores are compressed in a tablet press.

Next, the cores are coated with a semipermeable wall. The wall-forming composition comprises 20.8 mg of cellulose acetate having an acetyl content of 39.8%, 4.16 mg of poly(vinyl pyrrolidone) of 40,000 number-average molecular weight, and 1.04 mg of polyethylene glycol of 3,350 viscosity-average molecular weight. The wall-forming composition is applied as 4% solid from an acetone:methanol cosolvent (80:20 v:v). A pan coater is used to apply the wall around the cores. Two exit passageways are drilled in the semipermeable wall, and then the solvent is evaporated in an oven.

Next, the delivery system comprising the semipermeable wall is coated with an overcoat. The overcoat comprises a colorant for instant release of the colorant into a nutrient fluid. The overcoat comprises 8.8 mg of FD&C Blue Dye No. 1, 24.2 mg of mannitol, 4.4 mg of hydroxypropylmethylcellulose of 11,200 molecular weight, and 6.6 mg of polyethylene glycol of 3,350 weight-average molecular weight. The coating solution comprises 10% solid content in a water solvent. The solution is added to a pan coater and the overcoat is coated onto the exterior surface of the semipermeable wall. In a further manufacturing embodiment, the exit passageway can be provided after the overcoat is applied to the delivery system. The delivery system has a mean release rate of 9–10 mg/hr for 24.6 hours.

EXAMPLE 7

This example provides a composition of matter comprising a delivery system and an enteral nutritional formulation, wherein the delivery system comprises an overcoat comprising means for containing and instantly releasing a colorant to an enteral nutritional formulation, which is coated over a semipermeable wall that surrounds a core comprising a colorant, with exit means in the wall for delivering the colorant over a prolonged time to the enteral nutritional formulation that comprises 12 to 18 g of protein, 7 to 12 g of fat, and 35 to 47 g of carbohydrate, in an aqueous fluid for enteral nutritional support.

EXAMPLE 8

The enteral nutritional formulation according to Example 7, wherein the formulation comprises minerals and vitamins selected from the group consisting of calcium, phosphorus, potassium, sodium, chloride, magnesium, iron, zinc, copper, iodine, manganese, chromium, molybdenum, selenium, ascorbic acid, thiamine, riboflavin, niacin, biotin, pantothenic acid, pyridoxine, folic acid, cobalamin, vitamin A, vitamin D and vitamin E.

EXAMPLE 9

The nutritional formulation for enteral administration according to Example 7, wherein the nutritional formulation provides the daily nutritional requirements of minerals and vitamins selected from the group consisting of 0.8 to 1.2 g calcium, 0.8 to 1.2 g phosphorus, 2 to 5 g chloride, 2 to 5 g magnesium, 7 to 12 g iron, 12 to 18 g zinc, 1 to 5 g copper, 0.01 to 0.35 mg iodine, 1 to 7 mg manganese, 0.01 to 0.7 mg chromium, 0.10 to 0.5 mg molybdenum, 0.03 to 0.1 mg selenium, 40 to 80 mg ascorbic acid, 0.75 to 1.75 mg thiamine, 0.75 to 10 mg riboflavin, 12 to 25 mg niacin, 20 to 80 mg biotin, 1 to 10 mg pantothenic acid, 1 to 5 mg pyridoxine, 200 to 600 mg folic acid, 1 to 5 mg cobalamin, 750 to 1500 mg vitamin A, 2 to 15 mg vitamin D and 7 to 15 mg vitamin E.

EXAMPLE 10

A nutritional dispensing system comprising means for adding a colorant-dye to a nutrient is provided by a combination comprising a reservoir, a drip chamber, and a delivery system in the drip chamber. The reservoir is a container with means for adding a fluid to the reservoir, comprising an outlet means for letting a fluid exit the reservoir, and a capacity of 10 to 50,000 ml. The reservoir can be structured as a bottle or as a bag. The reservoir can be made of a member selected from the group consisting of glass and plastic. Acceptable materials for providing the reservoir as a flexible plastic bag include a polymer represented by a polyolefin, a polyethylene, a polyvinylchloride and a polytetrafluorethylene. The outlet of the reservoir connects through a releasable tube to a drip chamber. The drip chamber comprises a wall that surrounds an internal lumen with a capacity of 5 to 100 ml, an inlet for letting fluid enter the drip chamber, and an outlet for letting fluid exit the drip chamber. The drip chamber can be calibrated to deliver drops of 5, 10, 15, 20 or more per milliliter that pass through the drip chamber. A feeding tube connects releasably to the outlet and carries the nutrient to the patient. The reservoir and the drip chamber are described in *Intravenous Medications,* Sager and Bomar, pp. 3–153 (1980), J. B. Lippincott Co.

A delivery system provided by the invention that can be positioned inside the drip chamber comprises a core, comprising 50 wt % of FD&C Blue Dye No. 1, 29 wt % mannitol, 12 wt % potassium chloride, 3 wt % hydroxypropylmethylcellulose of 11,200 molecular weight, 1 wt % magnesium stearate, and 5 wt % hydroxypropylcellulose of 40,000 molecular weight; a wall comprising a semipermeable composition of 80 wt % cellulose triacetate, 16 wt % poly(vinyl pyrrolidone), and 4 wt % polyethylene glycol of 3,350 molecular weight; and an overcoat carried by the semipermeable wall, comprising 20 wt % FD&C Blue Dye No. 1, 55 wt % mannitol, 10 wt % hydroxypropylmethylcellulose, and 15 wt % polyethylene glycol. The dye is delivered through exit means at a controlled rate of 9.4 mg/hr up to 25 hours to a nutrient as it flows through the drip chamber.

EXAMPLE 11

A delivery system is prepared by following the above example, wherein the delivery system delivers a pharmaceutically acceptable and nutritionally compatible dye at a release rate of 0.5 to 25 mg/hr over 12 to 25 hours, and the semipermeable wall comprises 100 wt % cellulose acylate.

EXAMPLE 12

A delivery system for delivering a pharmaceutically acceptable dye to a nutritional support formulation is made according to the above examples and comprises: 255 mg of a pharmaceutically acceptable dye, 147.9 mg of a saccharide, 15.3 mg of a hydroxypropylalkylcellulose, 61.2 mg of an osmagent, 5.1 mg of a lubricant, and 25.5 mg of a hydroxyalkylcellulose; a wall comprising 20.8 mg of a cellulose polymer, 4.2 mg of poly(vinyl pyrrolidone) and 1.0 mg of a lubricant; and an overcoat consisting of 24.8 mg of a carbohydrate, 4.5 mg of a hydroxypropylalkylcellulose, 6.8 mg of polyethylene glycol, and 9.0 mg of a nontoxic dye.

EXAMPLE 13

The delivery system according to Example 12, wherein the compositional core in the delivery system weighs 510 mg, the wall weighs 26 mg and the overcoat weighs 45 mg.

EXAMPLE 14

A delivery system for delivering a colorant to a fluid nutritional formulation is made as follows: First, 255 mg of FD&C Blue Dye No. 1 is blended with 147.9 mg mannitol, 61.2 mg potassium chloride, 15.3 mg hydroxypropylmethylcellulose of 11,200 number-average molecular weight and 25.5 mg hydroxypropylcellulose of 40,000 number-average molecular weight, with all the ingredients blended to yield a homogenous mass. Then, ethanol is added to the mass and the blending continued to yield a wet mass. The wet mass is screened and dried to granules. The granules are mixed with 5.1 mg of lubricant magnesium stearate, and cores are compressed in a tablet press.

Next, the cores are coated with a semipermeable wall. The wall-forming composition comprises 20.8 mg cellulose acetate having an acetyl content of 39.8%, 4.2 mg poly(vinyl pyrrolidone) of 40,000 number-average molecular weight and 1.0 mg polyethylene glycol of 3,350 weight-average molecular weight. The wall-forming composition is applied as 4% solid from an acetone:methanol cosolvent (80:20 v:v). A pan coater is used to apply the wall around the cores. Two exit passageways are drilled in the semipermeable wall, and then the solvent is evaporated in an oven.

Next, the delivery system comprising the semipermeable wall is coated with an overcoat. The overcoat comprises a colorant for instant release of the colorant into a nutrient fluid. The overcoat comprises 9 mg of FD&C Blue Dye No. 1, 24.8 mg of mannitol, 4.5 mg of hydroxypropylmethylcellulose of 11,200 molecular weight, and 6.8 mg of polyethylene glycol of 3,350 weight-average molecular weight. The coating solution comprises 10% solid content in a water solvent. The solution is added to a pan coater and the overcoat is coated onto the exterior surface of the semipermeable wall. In a further manufacturing embodiment, the exit passageway can be provided after the overcoat is applied to the delivery system. The delivery system has a mean release rate of 9–10 mg/hr for 24.6 hours.

EXAMPLE 15

A process is disclosed in this example for adding a color to a nutritional formulation. The process is as follows: First, a reservoir-container, comprising 1,000 ml of an aqueous-based fluid formulation that supplies to a patient 0.8 to 1.5 g/kg of protein (per body weight), 15 to 175 meg/kg of sodium, 10 to 150 meg/kg of potassium, 10 to 175 meg/kg of chloride, 5 to 20 meg/kg of calcium, 5 to 25 meg/kg of phosphorus, 5 to 30 meg/kg of magnesium, 3 to 10 meg/kg of zinc, and 0.5 to 15 meg/kg of copper, which reservoir-container is connected in releasable connection through a tube to the inlet of a drip chamber. Then, a delivery system is added to the drip chamber, the delivery system comprising: (1) a core, comprising 20 to 70 wt % of a dye; 10 to 40 wt % of a carbohydrate selected from the group consisting of: a saccharide, sucrose, glucose, fructose, mannitol, mannose, galactose, aldohose, aldopentose, allose, altrose, talose, gulose and idose; 2 to 30 wt % of a hydroxypropylalkylcellulose of 9,200 to 125,000 molecular weight; 5 to 25 wt % of an osmagent selected from the group consisting of sodium chloride, potassium chloride, magnesium sulfate, magnesium chloride, potassium sulfate, sodium sulfate, lithium sulfate and magnesium succinate; 0.5 to 5 wt % of a lubricant such as magnesium stearate, potassium stearate or stearic acid; and 0.5 to 12 wt % of a hydroxyalkylcellulose of 30,000 to 50,000 molecular weight; (2) a wall surrounding the core, comprising: 40 to 90 wt % of a member selected from the group consisting of cellulose ester, cellulose ether and cellulose ester-ether, 5 to 25 wt % of poly(vinyl pyrrolidone) of 15,000 to 75,000 molecular weight, and 0.5 to 8 wt % of a polyethylene glycol of 2,000 to 5,000 molecular weight; (3) an overcoat, comprising 10 to 30 wt % of a dye, 35 to 75 wt % of a carbohydrate, 4 to 18 wt % of a hydroxypropylalkylcellulose of 9,200 to 75,000 molecular weight, and 5 to 20 wt % of a polyethylene glycol of 2,000 to 5,000 molecular weight, with the total weight equal to 100 wt %; and (4) an exit orifice through the overcoat and the wall for delivering the dye to nutritional fluid flooring through the drip chamber over 24 hours.

EXAMPLE 16

The procedure is followed in the above example to provide a delivery system that releases FD&C Blue Dye No. 1 at a rate of 0.14 mg/min over 24 hours.

EXAMPLE 17

The procedures of the above examples are followed for providing delivery systems encompassing all shapes useful for the purpose of this invention. The delivery systems provided by this invention comprise a plurality of shapes, including square, rectangular, round, oblong, ellipse, bulbous, bean, tablet and capsule. The delivery system includes any shape that readily lends itself to placement within a drip chamber and permits the free passage or flow of fluid into, through, and out of the drip chamber. The delivery system embraces a shape that does not block the fluid outlet, during use it remains in the drip chamber, its shape avoids passage into the outlet, and its shape avoids passage into a patient.

METHOD OF PRACTICING THE INVENTION

The invention provides a method for delivering a formulation comprising a nutrient and a fluid to a patient in need of a nutritional support formulation. The method comprises: (A) admitting into the gastrointestinal tract of the patient a nutritional support system comprising: (1) a reservoir, comprising an outlet and an inlet, and a nutritional formulation comprising a nutrient and a pharmaceutically acceptable liquid; and (2) a drip chamber, comprising an inlet and an outlet, with the inlet releasably communicating through a tube with the outlet of the reservoir, and the drip chamber outlet releasably communicating through a tube with the patient; and (B) administering the formulation comprising the nutrient and the fluid in a beneficially effective amount over a prolonged period of time; and wherein the method is characterized by (3) a delivery system in the drip chamber that adds a dye to a nutritional formulation that enters the drip chamber, which delivery system comprises a core containing 20 to 70 wt % of a dye, 10 to 40 wt % of a saccharide, 2 to 30 wt % of a hydroxypropylalkylcellulose, 5 to 25 wt % of an osmagent, 0.5 to 5 wt % of a lubricant, and 0.5 to 12 wt % of a hydroxyalkylcellulose; a wall that surrounds the core and comprises 40 to 90 wt % of a cellulose polymer, 5 to 25 wt % of a poly(vinyl pyrrolidone) and 0.5 to 8 wt % of a polyethylene glycol, and an exit in the delivery system for delivering the dye to formulation that enters the drip chamber.

The invention provides for the use of a nutritional support system for administering a nutritional formulation to a patient, wherein the nutritional system comprises: (A) a reservoir, comprising a wall that surrounds an internal lumen, with an outlet in the wall for letting a nutritional formulation leave the reservoir; (B) a drip chamber, comprising an internal lumen with an inlet and an outlet, with the inlet releasably connected to the outlet of the reservoir; and (C) conveying means releasably connected to the outlet of the drip chamber for conveying a nutritional formulation to the patient; and wherein the reservoir is characterized by containing a nutritional formulation comprising water, proteins, minerals, saccharides and vitamins; and the drip chamber is characterized by containing a delivery system comprising a dye, an osmotically active compound, and a member selected from the group consisting of a hydroxyalkylcellulose and a hydroxypropylalkylcellulose; a wall comprising a cellulose polymer; and an exit in the delivery system for delivering the dye to the nutritional formulation that enters the drip chamber.

The above disclosure and examples present the invention for gastrointestinal administration of a nutritional support formulation. The invention, however, embraces adaptations of the nutritional support system for administering a nutritional support formulation intravenously, parenterally, and intraperitoneally.

The present invention provides many advantages to the nutritional art as described in the accompanying specification. Obviously, many modifications and variations of the instant invention are possible in light of the above specificity, and it is therefore to be understood that within the scope of the disclosure and the appendix claims, the invention may be practiced otherwise then is described specifically herein.

What is claimed is:

1. A drip chamber comprising: a wall that surrounds an internal space: an inlet for admitting a nutritional formulation into the drip chamber, and an outlet for letting the nutritional formulation leave the drip chamber: a delivery system in the internal space for delivering colorant dye into the nutritional formulation comprising a composition comprising: 20 to 70 wt % of a dye suitable for delivering colorant into said nutritional formulation, 10 to 40 wt % of a carbohydrate, 2 to 30 wt % of a hydroxypropylalkylcellulose of 9,200 to 125,000 molecular weight, 5 to 25 wt % of an osmagent, 0.5 to 5 wt % of a lubricant, and 0.5 to 12 wt % of a hydroxyalkylcellulose of 30,000 to 50,0000 molecular weight; a wall that surrounds the composition and comprises 40 to 90 wt % of a member selected from the group consisting of a cellulose ester, cellulose ether and cellulose ester-ether, 5 to 25 wt % of a poly(vinyl pyrrolidone) of 15,000 to 75,000 molecular weight, and 0.5 to 8 wt % of a polyethylene glycol of 2,000 to 5,000 molecular weight; and overcoat on the wall comprising 10 to 30 wt % of a dye, 35 to 75 wt % of a carbohydrate, and 4 to 18 wt % of a hydroxypropylalkylcellulose of 9,200 to 75,000 molecular weight and 5 to 20 wt % of a polyethylene glycol of 2,000 to 5,000 molecular weight; and exit means in the delivery system for delivering the composition over a prolonged period of time.

* * * * *